United States Patent
Lim

(10) Patent No.: US 9,359,423 B2
(45) Date of Patent: Jun. 7, 2016

(54) PROTEIN INVOLVED IN DETECTION OF CANCER METASTASIS AND A TREATMENT THEREOF

(75) Inventor: Yoon Pin Lim, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 14/240,798

(22) PCT Filed: Aug. 24, 2012

(86) PCT No.: PCT/SG2012/000301
§ 371 (c)(1),
(2), (4) Date: Feb. 25, 2014

(87) PCT Pub. No.: WO2013/028137
PCT Pub. Date: Feb. 28, 2013

(65) Prior Publication Data
US 2014/0199330 A1   Jul. 17, 2014

(30) Foreign Application Priority Data

Aug. 25, 2011   (SG) .................................. 201106166

(51) Int. Cl.
| | | |
|---|---|---|
| *C12N 15/11* | (2006.01) | |
| *C12N 15/113* | (2010.01) | |
| *C07K 14/705* | (2006.01) | |
| *G01N 33/574* | (2006.01) | |
| *C12Q 1/68* | (2006.01) | |
| *C07K 16/30* | (2006.01) | |
| *A61K 39/00* | (2006.01) | |

(52) U.S. Cl.
CPC ........... *C07K 14/705* (2013.01); *C07K 16/3015* (2013.01); *C12N 15/1138* (2013.01); *C12Q 1/6886* (2013.01); *G01N 33/57415* (2013.01); *G01N 33/57492* (2013.01); *A61K 39/00* (2013.01); *C12N 2760/18522* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 6,852,318 | B1 * | 2/2005 | Varner .................... | A61K 38/08 424/130.1 |
| 2004/0180002 | A1 * | 9/2004 | Young .................... | C07K 16/00 424/1.49 |
| 2004/0197328 | A1 * | 10/2004 | Young .............. | A61K 47/48569 424/141.1 |

FOREIGN PATENT DOCUMENTS

WO   WO 2009/149239 A1 * 12/2009 ............. A61K 37/70

OTHER PUBLICATIONS

Gura (Science, 1997, 278:1041-1042).*
Kaiser (Science, 2006, 313: 1370).*
Fiorio Pla et al., TRPV4 mediates tumor-derived endothelial cell migration via arachidonic acid-activated actin remodeling. Oncogene. Jan. 12, 2012;31(2):200-12. Epub Jun. 20, 2011.
Gkika et al., Molecular mechanisms of TRP regulation in tumor growth and metastasis. Biochim Biophys Acta. Jun. 2009;1793(6):953-8. Epub Dec. 6, 2008.
Ho et al., Novel breast cancer metastasis-associated proteins. J Proteome Res. Feb. 2009;8(2):583-94.
Liu et al., Inhibition of the expression and function of TRPV4 by RNA interference in dorsal root ganglion. Neurol Res. Jun. 2011;32(5):466-71. Epub Mar. 11, 2009.

* cited by examiner

*Primary Examiner* — Peter J Reddig
(74) *Attorney, Agent, or Firm* — Wolf, Greenfield & Sacks, P.C.

(57) ABSTRACT

Using phosphoproteomics, we profiled the phosphorylation levels of hundreds of proteins concurrently across an isogenic model of breast cancer metastasis. Among them is TRPV4, a calcium channel that we found to be overexpressed in invasive breast tumors compared to ductal carcinoma in situ, a pre-neoplastic lesion and normal tissues. TRPV4 was also found to be elevated mostly in invasive breast cancer cell lines and less so in non-invasive breast cancer cell lines. These data led us to hypothesize that TRPV4 confer early traits of metastatic cancer cells. Functional studies revealed that silencing of TRPV4 expression diminished breast cancer cell migration and invasion significantly but not proliferation. Silencing expression of TRPV4 in metastatic breast cancer cells also reduced the number and size of metastatic colonies in mice. This supports the notion that TRPV4 is an attractive drug target to curb metastasis. Further experimentations suggested that the functional effect of TRPV4 on breast cancer cellular processes was associated with regulation of intracellular Ca2+, cell plasticity and expression of cell-cell adhesion proteins such as beta-catenin and E-cadherin. The latter two events have obvious implications in cancer invasion and intravasation/extravasation. We have also made novel observations that activation of TRPV4 by PDD led to activation of AKT and FAK pathways, both shown to be important to cell migration. In particular, downregulation of E-cadherin and b-catenin following TRPV4 activation has been shown to be mediated by the AKT pathway. Collectively, our data suggest that activation of Ca2+ dependent cascades and pathways associated with cell migration mediate TRPV4 function in breast cancer metastasis.

4 Claims, 9 Drawing Sheets

PROTEIN INVOLVED IN DETECTION OF CANCER METASTASIS AND A TREATMENT THEREOF

CROSS-REFERENCE TO RELATED APPLICATION

This application is a national stage filing under 35 U.S.C. §371 of international application No. PCT/SG2012/000301, filed 24 Aug. 2012, which was published under PCT Article 21(2) in English, and claims benefit of, and priority from, Singapore patent application No. 201106166-0, filed on 25 Aug. 2011, the contents of each of which are hereby incorporated herein by reference.

FIELD OF THE INVENTION

The present technology relates to a cancer biomarker and drug target and a method of detecting or prognosing or treating cancer, particularly breast cancer metastasis.

BACKGROUND

Worldwide breast cancer is the second most common type of cancer and one of the most common causes of cancer death in humans. It is the most common cancer in women and makes up a third of cancer occurrence of women in the US. Common tests that provide information to assists in the diagnosis or prognosis of breast cancer include mammograms and tissue biopsy followed by combinations of histological examination, immune-histochemical detection with antibodies to estrogen receptor (ER), progesterone receptor (PR) and/or HER2/neu proteins.

Current treatment of breast cancer includes surgery, chemotherapy, radiation therapy and immunotherapy. Targeted therapy such as HER2/neu antibody first became available in the late 1990's. Other targeted therapies involve either blocking estrogen or the estrogen receptor. Estrogen is implicated in initiation and progression of breast cancer growth. Progesterone therapy is often used to block estrogen. Estrogen receptor antagonists such as tamoxifen and raloxifene have been used to treat breast cancer. Research shows that Tamoxifen becomes ineffective in 35% of patients taking the drug particularly where the breast cancer has metastasized.

Metastasis is a complex series of steps in which neoplasic cells leave the original tumor site and migrate to other parts of the body via the blood stream or the lymphatic system and start new tumors that resemble the primary tumor. Breast cancer cells are often transported through the lymphatic pathway to bone or other areas such as liver, lung or brain. It may be life saving to predict whether a primary cancer has the potential to metastasize such that high risk patients can be subject to closer follow up or specific treatment regime that will vary where the cancer has metastasized. Currently there is no way to visualize metastatic tumors so that effectiveness of therapy can be more easily monitored. Currently, detection of metastatic sites requires numerous, time consuming and costly tests that does not have very high specificity.

Transient receptor potential cation channel subfamily V member 4 TRPV4 is a protein that in humans is encoded by the TRPV4 gene. The TRPV4 protein is a member of the OSM9-like transient receptor potential channel (OTRPC) subfamily in the transient receptor portential (TRP) superfamily of ion channels. The encoded protein is a $Ca^{2+}$-permeable, nonselective cation channel that is thought to be involved in the regulation of systemic osmotic pressure.

SUMMARY OF THE INVENTION

The present invention seeks to provide novel methods of detecting, predicting and/or compounds for treating cancer metastasis such as breast cancer to ameliorate some of the difficulties with the current detection, prediction of metastasis and treatment.

We have discovered a correlation between expression of TRPV4 polypeptide and breast cancer metastasis.

Accordingly the present invention provides a method of analysing a cell expression profile for determining whether the cell is metastatic comprising extracting the cell; Measuring an amount of TRPV4 nucleic acid or polypeptide in the cell; Comparing the amount of TRPV4 nucleic acid or protein present in the cell to the amount of TRPV4 nucleic acid or polypeptide in a sample isolated from normal, non-cancerous cells, wherein an amplified amount of TRPV4 nucleic acid or polypeptide in the cell relative to the amount of TRPV4 nucleic acid or polypeptide in the sample indicates that cancer is likely to metastasize; and wherein the absence of an amplified amount of TRPV4 nucleic acid or polypeptide in the cell relative to the amount of TRPV4 nucleic acid or polypeptide in the sample indicates that cancer is not likely to metastasize The present invention also provides a method of detecting a metastatic state of breast cancer comprising the steps of: measuring the amount of TRPV4 nucleic acid or polypeptide in the first biological sample extracted from a location distant from a breast tumour; and Comparing the amount of TRPV4 nucleic acid or polypeptide in the first sample with the amount of TRPV4 nucleic acid or polypeptide in a second biological sample isolated from normal, non-cancerous cells, wherein an amplified amount of TRPV4 nucleic acid or polypeptide in the first biological sample relative to the amount of TRPV4 nucleic acid or polypeptide in the second biological sample indicates the presence of metastatic cancer wherein the absence of an amplified amount of TRPV4 nucleic acid or polypeptide in the first biological sample relative to the amount of TRPV4 nucleic acid or polypeptide in the second biological sample indicates the absence of metastatic cancer.

The present invention also provides an antibody capable of binding selectively a TRPV4 polypeptide set out in sequences listed Another aspect of the invention provides an immunhistochemical method for measuring expression of a TRPV4 polypeptide in a test tissue section extracted from a tumour comprising: incubating the test tissue section with the antibody of the invention under conditions which allow for the formation of an antibody-antigen complex; staining the antibody-antigen complex of the test tissue section with a reagent; and analyzing the test tissue section to quantify an amount of the stained antibody-antigen complex in the test tissue section; wherein an amplified amount of the stained antibody-antigen complex relative to the amount of the stained antibody-antigen complex in a tissue section taken from normal, non-cancerous tissue indicates that the breast cancer has the tendency to metastasize; and wherein the absence of an amplified amount of the stained antibody-antigen complex relative to the amount of the stained antibody-antigen complex in a tissue section taken from normal, non-cancerous tissue indicates the breast cancer has no tendency to metastasize.

The present invention also provides a method of treating breast cancer metastasis comprising administering to a patient in need of therapy an antagonist to TRPV4 nucleic acid expression or polypeptide.

The present invention also provides a composition comprising a therapeutically effective amount of an inhibitor of TRPV4 polynucleotide expression or polypeptide in cells.

The present invention also provides a kit for detecting breast cancer in cells comprising a reagent for detecting TRPV4 polynucleotide expression; a buffer and instructions for predicting whether breast cancer cells have metastasized.

The present invention further provides method for screening for antagonists of TRPV4 polynucleotide expression comprising contacting a cell expressing TRPV4 polynucleotide with a sample compound; and measuring the amount of TRPV4 polynucleotide expression in both the presence and absence of the sample compound; wherein a decrease in TRPV4 polynucleotide expression in the presence of the sample compound in relation to the TRPV4 polynucleotide expression in the absence of the sample compound indicates the sample compound is the antagonist.

The present invention further provides a method of making an antibody specific for TRPV4 polypeptide comprising isolating a TRPV4 polypeptide from a metastatic breast cancer; conjugating a TRPV4 polypeptide to a carrier protein; inducing production of an antibody of the TRPV4 polypeptide—carrier protein conjugate in a cell; and obtaining the antibody from the cell The present invention further provides a vaccine for treating metastatic breast cancer comprising a TRPV4 polypeptide.

The present invention also provides a method of treating breast cancer metastasis comprising administering to a patient in need of therapy a vaccine of the invention.

Another aspect of the invention provides a method of visualizing TRPV4 expression on a cell surface comprising the steps of administering an antibody capable of binding selectively a TRPV4 polypeptide, the antibody conjugated to a reporter.

Another aspect of the invention comprises a method of measuring a copy number of TRPV4 nucleic acid wherein an increased copy number of TRPV4 nucleic acid indicates a cancer has metastasised.

Other aspects and advantages of the invention will become apparent to those skilled in the art from a review of the ensuing description, which proceeds with reference to the following illustrative drawings of preferred embodiments.

DETAILED DESCRIPTION OF THE PREFERRED EMBODIMENTS

Figure 1:
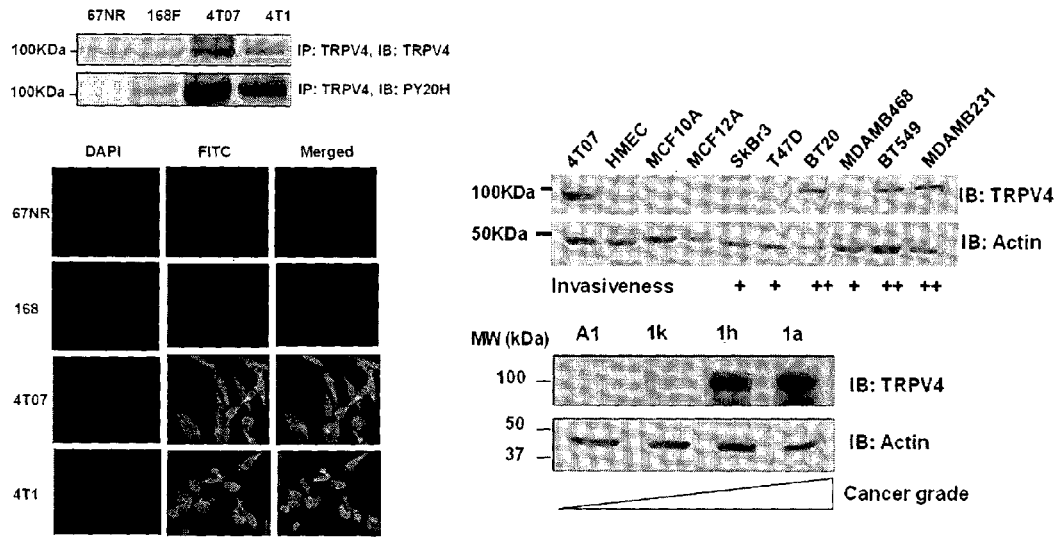
FIG. 1—Left panel: validation of the upregulation of TRPV4 across the breast cancer metastasis model using immunoblotting and immunofluorescence. Right panel: Expression of TRPV4 in invasive breast cancer cell lines but not non-invasive or normal breast mammary epithelial cell lines.
Figure 2A:
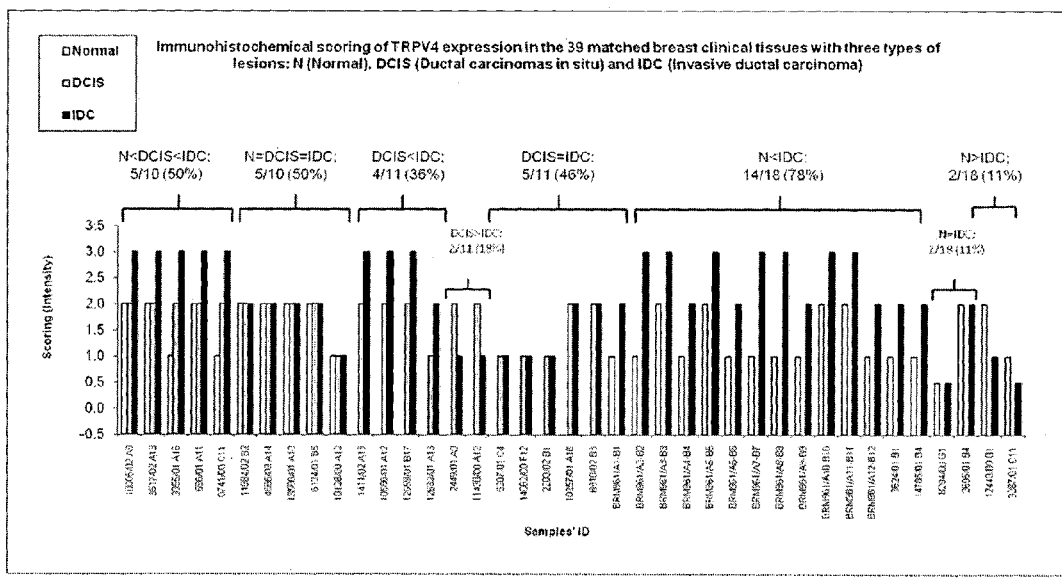
FIG. 2A—IHC of TRPV4 in matched normal, ductal carcinoma in situ and invasive carcinoma tissues of the breast. 2B-Immunohistochemistry showing the average expression of TRPV4 in normal tissues, ductal carcinoma in situ, invasive and metastatic lesions.
Figure 2B:
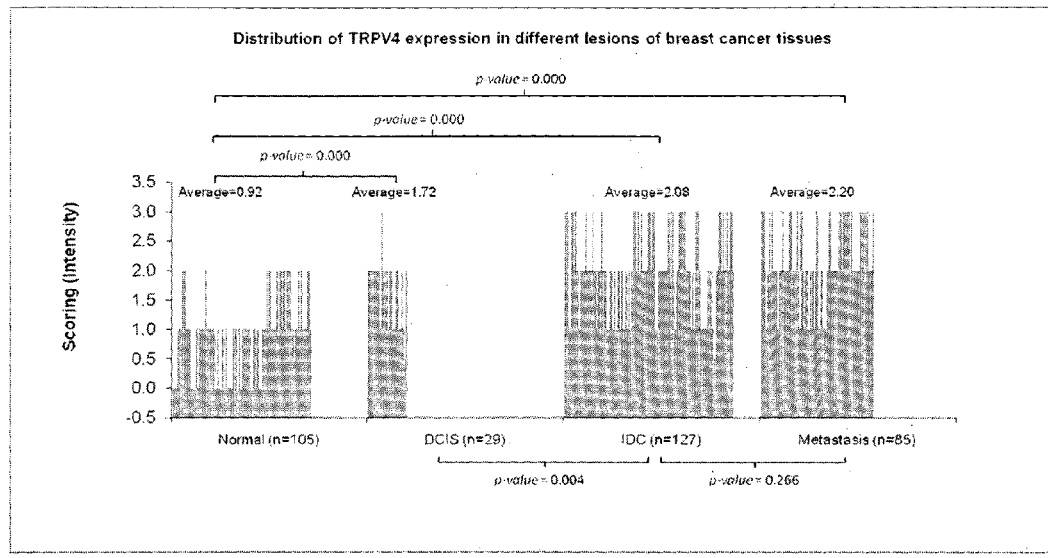
Figure 3A:
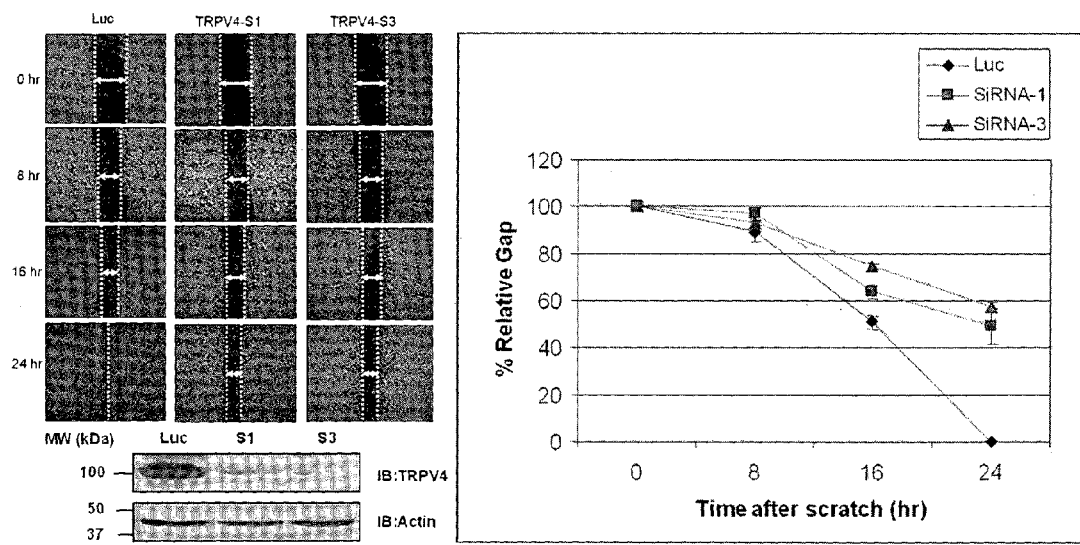
FIG. 3A—Silencing of TRPV4 expression reduced breast cancer cell migration. 3B—Silencing of TRPV4 expression reduced breast cancer cell chemotaxis. 3C—Silencing of TRPV4 expression reduced breast cancer invasion. 3D—Silencing of TRPV4 expression reduced breast cancer cell transendothelial migration. 3E—Silencing of TRPV4 expression reduced breast cancer cell plasticity as judged by the reduced ability of the cells to form blebs when cells were subject to micropipette aspiration. 3F—Silencing of TRPV4 expression reduced breast cancer cell plasticity as judged by the lower amount of pressure required to cause blebbings (membrane protrusions).
Figure 3B:
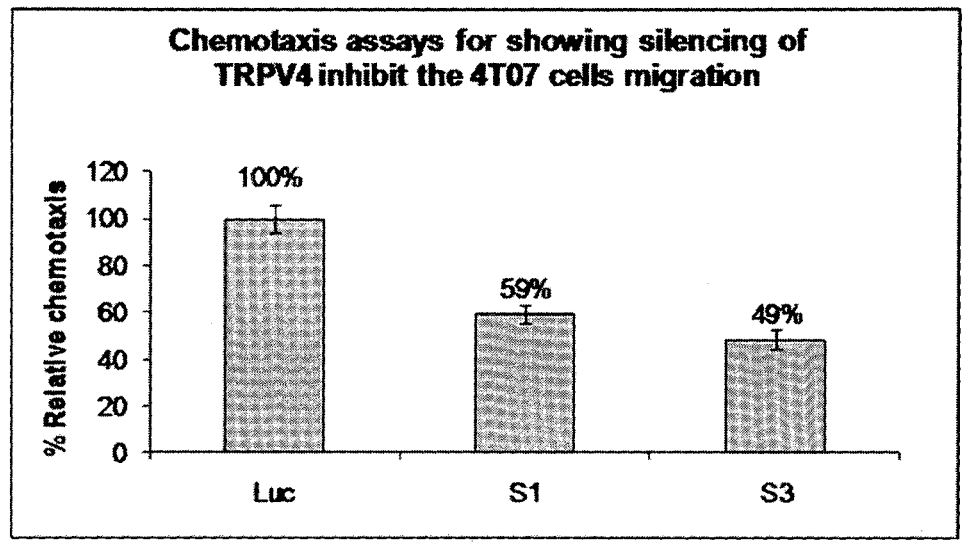
Figure 3C:
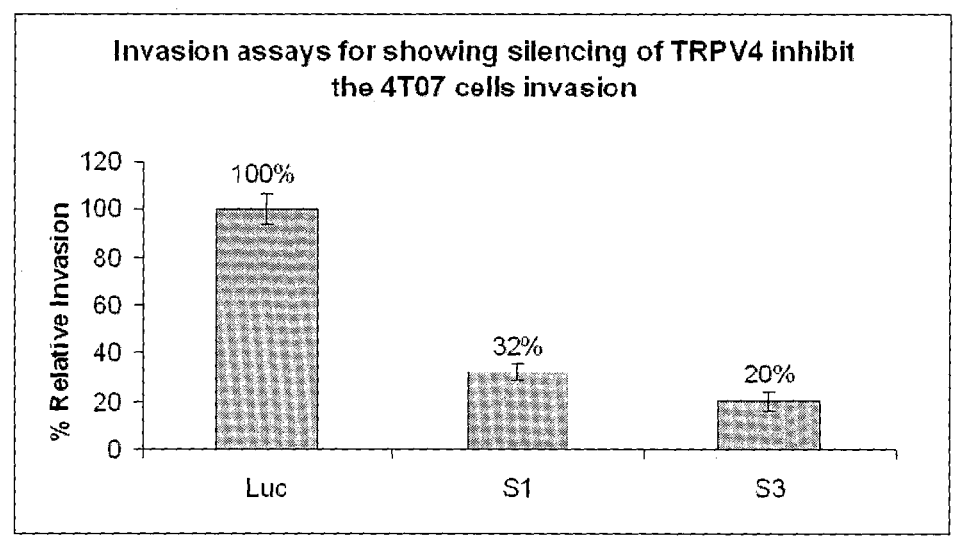
Figure 3D:
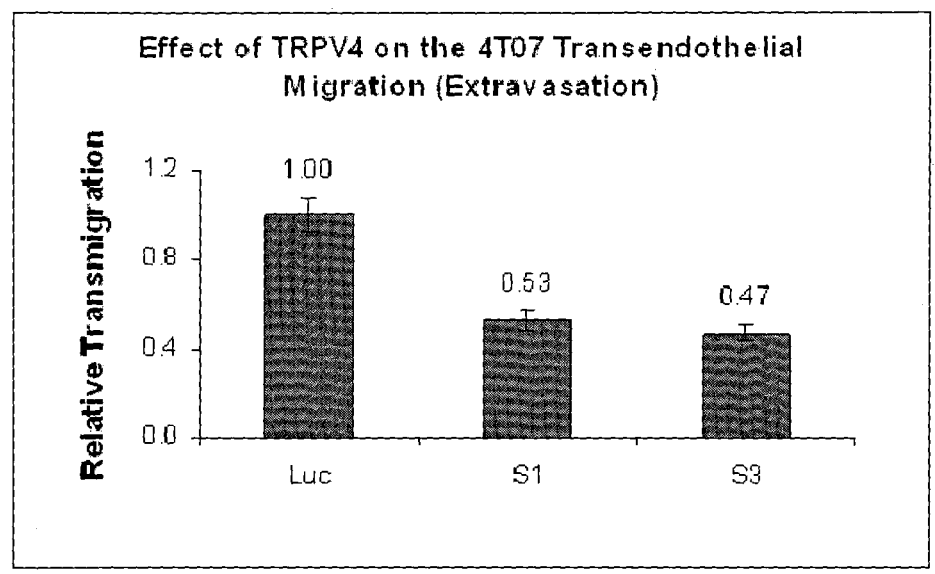
Figure 3E:
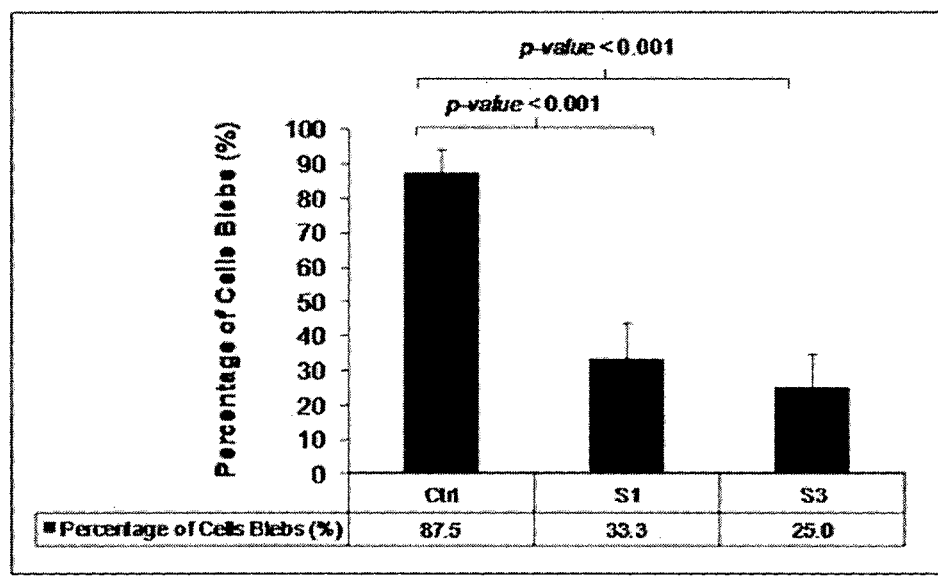
Figure 3F:
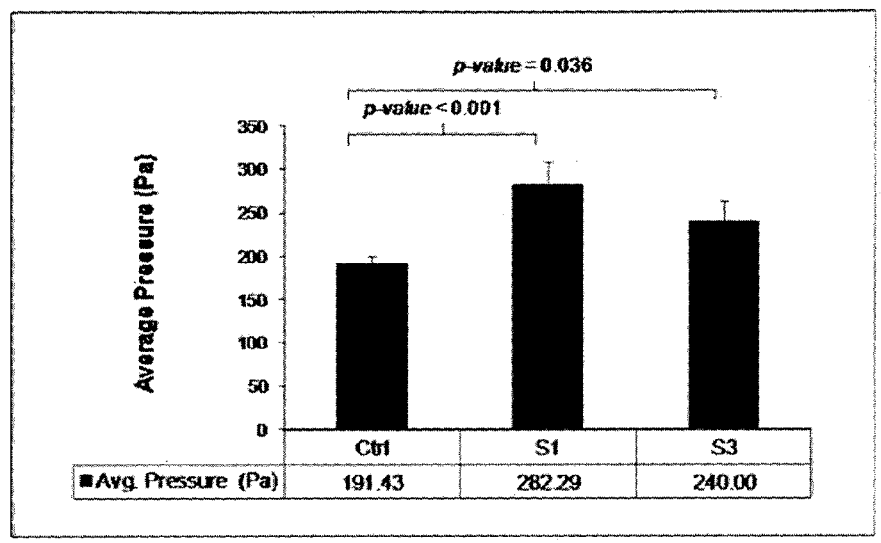
Figure 4A:
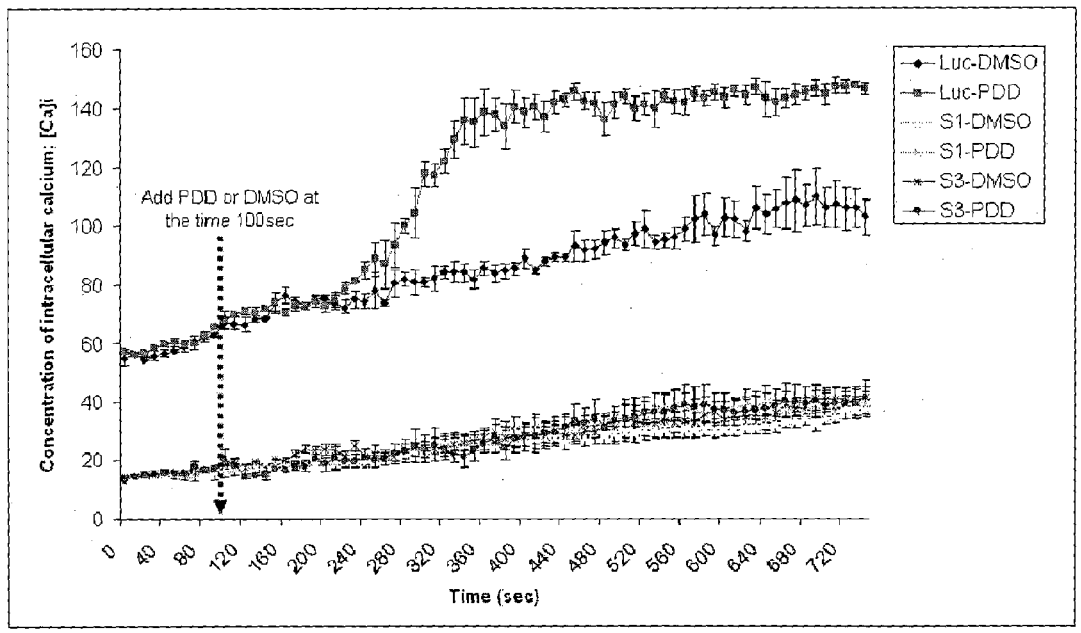
FIG. 4A—Silencing of TRPV4 expression was associated with a failure to produce a rise of intracellular Ca2+ upon stimulation with PDD. 4B—Activation of TRPV4 by PDD treatment reduced expression of cell-adhesion proteins like E-cadherin, b-catenin and paxillin. 4C—Activation of TRPV4 by PDD treatment stimulated AKT, FAK and MAPK pathway.
Figure 4B:
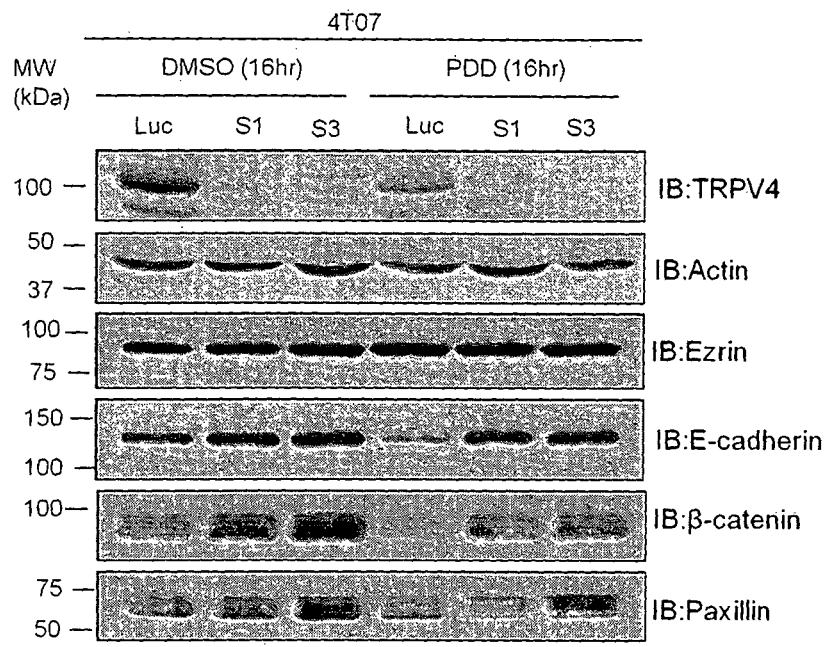
Figure 4C:
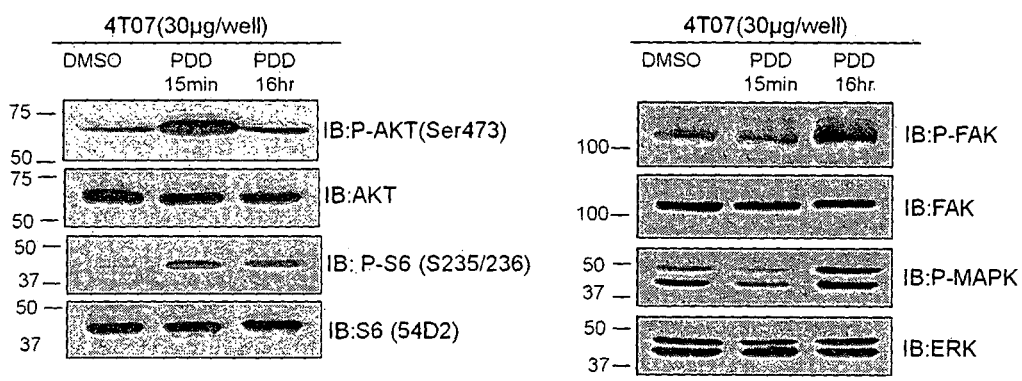
Figure 5:
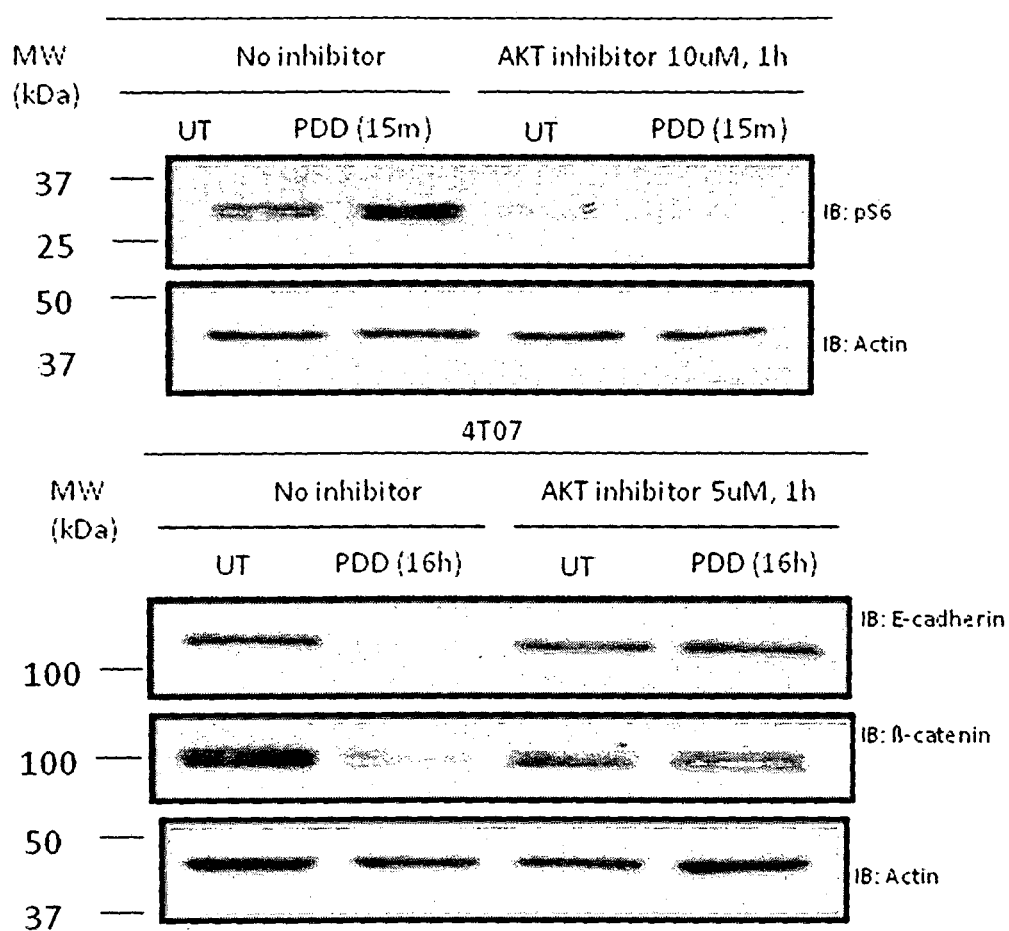
FIG. 5—AKT mediates TRPV4-induced downregulation of E-cadherin and b-catenin. Down regulation of these cytoskeletal proteins correlate with an increase in cancer cell plasticity required for intravasation and extravasation processes during metastasis. Cells were either treated or not treated with PDD (activator of TRPV4) in the presence or absence of AKT inhibitor). Top 1 and 2 panels, inhibition of AKT is confirmed by probing the phosphorylation status of S6, a downstream target of AKT. Bottom 3-5 panels, PDD-induced downregulation of E-cadherin and b-catenin.
Figure 6:
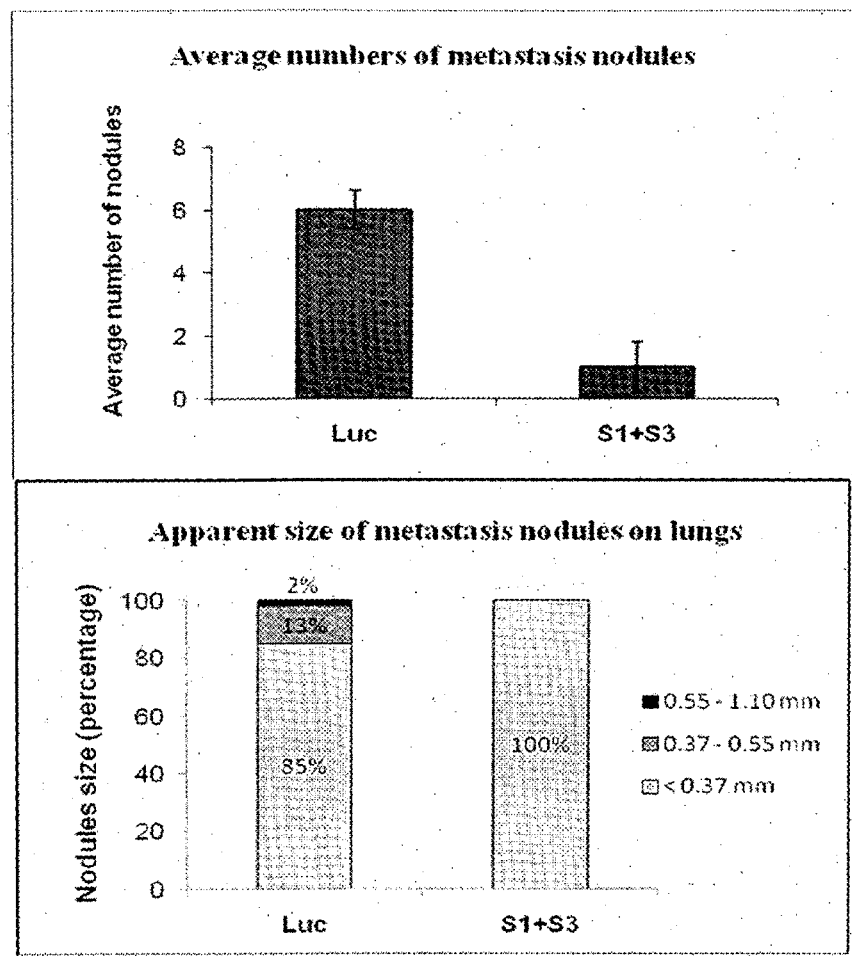
FIG. 6—Silencing the expression of TRPV4 reduced the number and size of metastatic colonies in mice. 4T1 metastatic cancer cells were transfected with control siRNA or TRPV4-specific siRNA before injected into the blood stream of mice via the tail vein. After about a week, mice were sacrificed and lungs (a common metastatic site for breast cancer) harvested and examined for metastatic colonies by a pathologist.
Figure 6:
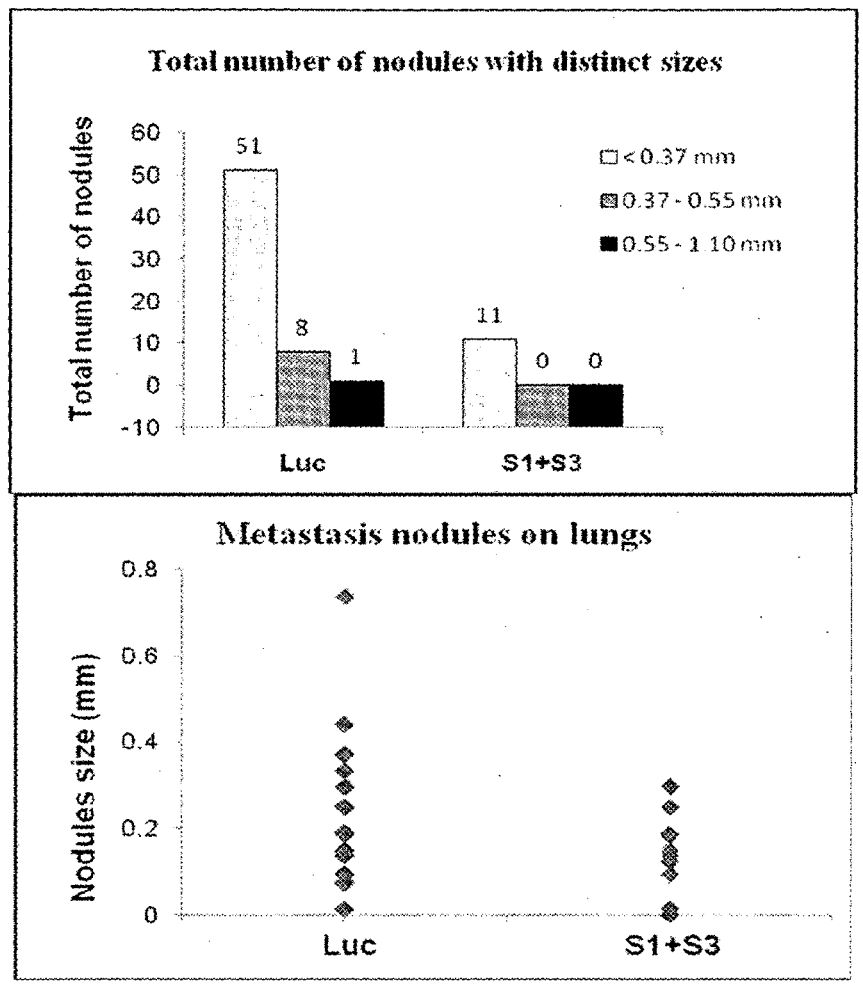

We conducted phosphorylation profiling of proteins across a biological model comprising 4 isogenic cell lines with increasing metastatic potential. Sixty phosphorylated proteins were confirmed to exhibit differential levels as breast cancer cells gained metastatic potential. TRPV4, a calcium channel protein, is for the first time shown to be elevated in breast cancer and regulated breast cancer cellular properties related to migration, invasion and metastasis.

According to the invention there is provided a diagnostic, or prognostic biomarker, TRPV4, capable of distinguishing between i) cancer and non cancer, ii) early and advanced/metastatic breast cancer and iii) detection and surveillance/monitoring of metastatic breast cancer during therapy. Antagonists to expression or activity of the TRPV4 polypeptide are able to decrease the metastatic traits of breast cancer both in vitro and in vivo providing compounds to treat cancer particularly breast cancer metastasis.

Preferably the method may further comprise bringing the nucleic acid into contact with a polynucleotide probe or primer comprising a polynucleotide sequence capable of hybridising selectively to the nucleotide sequence set out in the sequences or a fragment thereof under suitable hybridising conditions; and detecting any duplex formed between the probe or primer and nucleic acid.

In one embodiment the method may further comprise incubating a biological sample with the antibody under conditions which allow for the formation of an antibody-antigen complex; and determining whether an antibody-antigen complex comprising the antibody is formed.

Preferably the method may further comprise using an optical microscope, obtaining an image of the stained antibody-antigen complex in the test tissue section. Further the test tissue section may comprises a cell or plurality of cells suspected to be cancerous. Further the test tissue section may be fixed.

Preferably the reagent may be an antibody of the invention or a probe or primer comprising a polynucleotide sequence capable of hybridising selectively to the nucleotide sequence set out or a fragment thereof under suitable hybridising conditions.

Preferably the prognosis is a method of visualizing TRPV4 expression on a cell surface comprising the steps of administering an antibody capable of binding selectively a TRPV4 polypeptide, the antibody conjugated to a reporter such as a luminescent or fluorescent reporter or any other reporter known in the art that will report an antibody-antigen complex within a patient between the TRPV4 polypeptide and the antibody capable of binding selectively a TRPV4 polypeptide. The conjugated antibody is preferably administered into the patient's blood stream, that will detect TRPV4 on cell surface and aid in monitoring the site and size of tumor in various conditions. This would be suitable for prognosis either before or after treatment.

Preferably the method of treating breast cancer metastasis may further comprise administering a TRPV4 antagonist composition. Preferably the composition may be an antibody of the invention; or an interfering RNA; or a Calcium channel blocker specific to TRPV4 that has been used for clinical treatment of hypertension or know antagonists of TRPV4. Preferably the composition may be used in treating breast cancer or for the preparation of a medicament for the treatment of breast cancer.

In one embodiment a kit is provided for detection of the TRPV4 polypeptide. The kit may comprise an antibody of the invention or a probe or primer comprising a polynucleotide sequence capable of hybridising selectively to the nucleotide sequence set out or a fragment thereof under suitable hybridising conditions. Another embodiment is the conjugation of fluorescent dyes and nanoparticles to the detecting reagents for molecular imaging. In one embodiment the antibody of the invention is made in a cell, Preferably the cell may comprise a host animal induced by immunisation that may include an adjuvant or a hybridoma.

In one embodiment, TRPV4 has several domains that are important for its function. Mutations of TRPV4 that may affect its function in cancer biology described herein can be used as a biomarker for predicting metastasis or for prognostic or diagnostic purposes.

Accordingly, another aspect of the invention comprises a method of measuring a copy number of TRPV4 nucleic acid wherein an increased copy number of TRPV4 nucleic acid indicates a cancer has metastasised.

Preferably, the copy number of TRPV4 nucleic acid is measured using Fluorescence in situ hybridization (FISH). FISH allows visualization and mapping of the genetic material in an individual's cells, including TRPV4 gene or portions of the TRPV4 gene preferably having a sequence of SEQ ID NO.: 1. Unlike most other techniques used to study chromosomes, FISH does not have to be performed on cells that are actively dividing. This makes it a very versatile procedure. A technique used to identify the presence of specific chromosomes or chromosomal regions through hybridization (attachment) of fluorescently-labeled DNA probes to denatured chromosomal DNA. Examination under fluorescent lighting detects the presence of the hybridized fluorescent signal (and hence presence of the chromosome material) or absence of the hybridized fluorescent signal (and hence absence of the chromosome material). With metaphase FISH, cells progress through the division process until metaphase, when chromosomes are condensed and can be individually distinguished. In contrast to interphase FISH, metaphase FISH permits visualization of the actual chromosomes as well as the general location of the abnormality on the chromosome. Any other methods known in the art to measure the copy number of TRPV4 nucleic acid would also be suitable.

In one embodiment a vaccine is provided for treatment or prophylactics of metastatic breast cancer comprising a TRPV4 polypeptide. Preferably the vaccine may further comprise at least one suitable adjuvant.

Preferably the TRPV4 polypeptide of the vaccine may comprise a sequence set out or a homologue, variant, derivative or fragment thereof.

Preferably the vaccine may be used in treating breast cancer or for the preparation of a medicament for the treatment of breast cancer.

The technology consists of the following features:

The elevation of TRPV-4 in invasive and metastatic breast cancer cell but not normal and non-invasive/non-metastatic cells.

Without being limited to any particular theory the we consider the mechanism of TRPV-4 in metastatic breast cancer, to involve the activation of TRPV-4 results in the activation of AKT and FAK pathways, both shown to be important to cell migration.

TRPV4 activation led to reduction in cell/adhesion proteins such as E-cadherin/paxillin and beta-catenin relevant to cancer cell invasion and metastasis. We further show that the downregulation of E-cadhersin and b-catenin following TRPV4 activation is via the AKT pathway Silencing of TRPV4 expression in metastatic breast cancer cells reduced cancer cell migration, invasion and transendothelial migration in vitro. Silencing of TPRV4 also reduced the number and size of metastatic colonies in vivo, in mice. TRPV4 is a potential drug target for preventing metastasis. This is because silencing TRPV4 expression and hence function can block key processes associated with metastasis such as cell movement, invasion and transendothelial migration. Small molecules selective for TRPV4 exist and can block TRPV4 function. In addition, Calcium channel blockers that have been used for clinical treatment of hypertension may be useful anticancer drugs or at least to stop slow or diminish metastasis such breast cancer metastasis.

We discovered that TRPV4 expression is elevated in invasive/metastatic breast cancer cells compared to normal or non-invasive/metastatic breast cancer cells. TRPV4 is not expressed in all breast cancer cells but predominantly in invasive/metastatic breast cancer cells. We provided evidence for the role of TRPV4 in breast cancer epithelial cells. The present technology resides in the role of TRPV4 in breast cancer epithelial cells, in which the activation of TRPV4 results in (a) The activation of AKT and FAK pathways important for cell migration.
(b) The reduction in cell/adhesion proteins such as E-cadherin/paxillin and beta-catenin which are relevant to cancer cell invasion and metastasis because they correlate with cancer cell plasticity important for intravasation and extravasation processes during metastasis.

The Entrez Gene ID for TRPV4 is 59341 the known sequences can be found at http://www.ncbi.nlm.nih.gov/sites/entrez?db=gene&cmd=Retrieve&dopt=Graphics&list_uids=59341 and include SEQ ID NO. 2

In one embodiment inhibiting TRPV4 is in blocking metastasis and stopping or slowing the spread of cancer cells. The present technology focuses on the concept of blocking of TRPV4 is to reduce or prevent metastasis. A person using the present technology would test if it is working by detecting signs of cancer cells in other organs other than the primary site to determine if metastasis has been stopped, reduced blocked slowed or diminished.

Aberrations of proteins listed in Table 1 representing potential drug targets and biomarkers for breast cancer metastasis.

TRPV4 has been demonstrated to be upregulated in breast cancer compared to normal tissues. Over-expression of TRPV4 has also been demonstrated in early and late stage gastric cancer cells compared to normal cells supporting the notion that TRPV4 can be used as a biomarker for early detection of cancer, screening, cancer surveillance etc.

TRPV4 expression has been shown to be higher in invasive and metastatic lesions compared to pre-neoplastic lesion and normal cells. This implies that TRPV4 may be a risk factor that could be used to predictive metastasis and hence select patients for closer monitoring and aggressive treatment, thereby improving patients outcome.

Functional studies using RNAi revealed that TRPV4 expression is required for breast cancer cell migration, invasion and transendothelial migration (intravasation/extravasation). TRPV4 selective inhibitors exist. It is conceivable that TRPV4 is an attractive drug target for treatment of metastatic breast cancers.

Since Ca2+, AKT, FAK, MAPK and RhoA pathways have been shown to be components mediating TRPV4 function in breast cancer biology, these pathways are potential targets for therapeutic intervention alone or in combination with TRPV4.

Table 1 contains data from the first phosphoproteomics analysis of the isogenic model of breast cancer metastasis. For the first time, the levels of hundreds of phosphorylated proteins have been profiled and documented. Aberrations detected represented potential biomarker and drug targets. This is an important resource for basic and translational cancer research.

So far, there has been no report on the association of TRPV4 with breast cancer. TRPV4 may be a novel biomarker and drug target for metastatic breast cancer.

A diagnostic kit that detects TRPV4 could either be used for early detection of breast cancer, cancer surveillance and/or screening TRPV4 could serve as a biomarker alone or be included into existing panel of biomarkers to predict metastasis. This would improve clinical management of cancer.

Drugs against TRPV4 exist and can be tested as anti-cancer compounds in pre-clinical models before clinical trials.

The present technology can be used as diagnostic kit to detect breast cancer metastasis in patients, in predicting outcome and survival of breast cancer patients and possible drug target to block metastasis.

TRPV4 is a Ca2+ channel protein. RNAi-based approach for cancer therapy remains to show promise. Monoclonal antibodies may be an option since TRPV4 is a cell surface protein.

Antagonists

"Antagonist" to TRPV4 includes inhibitors and refers to anything that slows, blocks, or reduces the activity or expression of TRPV4. Similarly slows, blocks, or reduces cancer metastasis.

Antibodies

An antibody may include an immunoglobulin that specifically binds to the TRPV4 protein. The immunoglobulin may comprises an immunoglobulin heavy chain and/or an immunoglobulin light chain.

Preferably, the immunoglobulin is an IgG1 kappa immunoglobulin. most preferably; the immunoglobulin comprises a human IgG1 constant region within a heavy chain of said immunoglobulin and a human constant region within a light chain of said immunoglobulin. The immunoglobulin may comprise fully or partially human framework regions within the variable domain of said heavy chain and within the variable domain of said light chain. The immunoglobulin may comprise murine framework regions within the variable domain of said heavy chain and within said light chain.

The immunoglobulin wherein said immunoglobulin is conjugated to an agent selected from the group consisting of a therapeutic agent, a prodrug, a peptide, a protein, an enzyme, a virus, a lipid, a biological response modifier, a pharmaceutical agent, and PEG.

Polyclonal Antibodies

The antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant.

Typically, the immunizing agent and/or adjuvant will be injected in the mammal by multiple subcutaneous or intraperitoneal injections. The intensity of the response is determined by several factors including the size of the immunogen molecule, its chemical characteristics, and how different it is from the animal's own proteins. Most natural immunogens are proteins with a molecular weight above 5 kDa that come from sources phylogenically far removed from the host animal (i.e., human proteins injected into rabbits or goats). It is desirable to use highly purified proteins as immunogens, since the animal will produce antibodies to even small amounts of impurities present as well as to the major component. The antibody response increases with repeated exposure to the immunogen, so a series of injections at regular intervals is needed to achieve both high levels of antibody production and antibodies of high affinity.

To the extent that the antagonist is an antibody that engages the TRPV4 protein preventing cell migration, the immunogen will be selected from amino acids comprising the TRPV4 protein. Sequences of at least 5, 6, 7, 8, 9, 10, 15, 20, 25, 30 amino acids from this protein will generally be used to generate those antibodies. Desirably, the sequence selected will generate an antibody that specifically interferes with binding of TRPV4 to components of cell plasticity or cell-cell adhesion.

Not all immunogenic molecules will however generate the level of antibody desired. To increase the intensity of the immune response immunogens are combined with complex mixtures called adjuvants. Adjuvants are a mixture of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Examples of adjuvants which may be employed include Freund's complete adjuvant and MPL-TDM adjuvant (monophosphoryl Lipid A, synthetic trehalose dicorynomycolate).

If the immunogen is still unable to generate an acceptable response, it may be conjugated to a carrier protein that is more immunogenic. Small molecules such as drugs, organic compounds, and peptides and oligosaccharides with a molecular weight of less than 2-5 kDa like, for example, small segments if TRPV4, may not be immunogenic, even when administered in the presence of adjuvant. In order to generate an immune response to these compounds, it is necessary to attach them to a protein or other compound, termed a carrier that is immunogenic. When attached to a carrier protein the small molecule immunogen is called a hapten. Haptens are also conjugated to carrier proteins for use in immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore relevant to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Where the immunizing agent is a fibrinogen-like fragment segment such as from the c terminal preferably the fibrinogen-like fragment segment is conjugated to a protein known to be immunogenic in the mammal being immunized.

Examples of such immunogenic proteins include but are not limited to keyhole limpet hemocyanin (KLH), serum albumin, bovine thyroglobulin, soybean trypsin inhibitor, and a toxoid, for example tetanus toxoid.

KLH is a respiratory protein found in molluscs. Its large size makes it very immunogenic, and the large number of lysine residues available for conjugation make it very useful as a carrier for haptens. The phylogenic separation between mammals and molluscs increases the immunogenicity and reduces the risk of cross-reactivity between antibodies against the KLH carrier and naturally occurring proteins in mammalian samples.

KLH is offered both in its native form, for conjugation via amines, and succinylated, for conjugation via carboxyl groups. Succinylated KLH may be conjugated to a hapten containing amine groups (such as a peptide) via cross-linking with carbodiimide between the newly introduced carboxyl groups of KLH and the amine groups of the hapten.

Protocols for conjugation of haptens to carrier proteins are known.

The immunization protocol may be selected by one skilled in the art without undue experimentation. Protocols for preparing immunogens, immunization of animals, and collection of antiserum are also known.

Monoclonal Antibodies

The antibodies may, alternatively, be monoclonal antibodies. Monoclonal antibodies may be prepared using hybridoma methods, such as those known. In a hybridoma method, a mouse, hamster, or other appropriate host animal, is typically immunized with an immunizing agent as described above to elicit lymphocytes that produce or are capable of producing antibodies that will specifically bind to the immunizing agent. Alternatively, the lymphocytes may be immunized in vitro.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies.

The culture medium in which the hybridoma cells are cultured can then be assayed for the presence of monoclonal antibodies directed against TRPV4 or sequence SEQ ID No. 2.

After the desired hybridoma cells are identified, the clones may be subcloned by limiting dilution procedures and grown by standard methods. Suitable culture media for this purpose include, for example, Dulbecco's Modified. Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those known.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art.

Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding sub-sequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the methods known by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Bispecific Antibodies

Bispecific antibodies are monoclonal, preferably human or humanized, antibodies that have binding specificities for at least two different antigens. In the present case, one of the binding specificities is for TRPV4 and/or a segment of TRPV4, the other one is for another compound interacting with cell migration.

Methods for making bispecific antibodies are known in the art. Traditionally, the recombinant production of bispecific antibodies is based on the co-expression of two immunoglobulin heavy-chain/light-chain pairs, where the two heavy chains have different specificities.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and others known to a person skilled in the art.

Immunoconjugates

The invention also pertains to immunoconjugates comprising an antibody conjugated to a cytotoxic agent such as a chemotherapeutic agent, toxin (e.g., an enzymatically active toxin against hemagglutinin), or a radioactive isotope (i.e., a radioconjugate).

Conjugates of the antibody and cytotoxic agent are made using a variety of bifunctional protein-coupling agents such as N-succinnimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Alternatively, the conjugate may comprise the antibody capable of binding selectively a TRPV4 polypeptide, and a reporter. The reporter may be a luminescent or fluorescent reporter such as a GFP or any other reporter known in the art that will report an antibody-antigen complex within a patient between the TRPV4 polypeptide and the antibody capable of binding selectively a TRPV4 polypeptide.

Antisense Technology

Antisense technology, includes sequence-specific DNA oligomers; small-interfering RNA (siRNA); or Phosphorodiamidate Morpholino. Any gene silencing mechanism of antisense analogs such as siRNAs and shRNAs that interfere with the cellular transcription of TRPV4 RNA and activate RNase H to mediate RNA degradation would be suitable. Similarly sequence-specific TRPV4 morpholinos with a high affinity to bind to complementary TRPV4 target sequence in the untranslated region (UTR) or to the sequence near or overlapping the AUG translational start codon of the RNA strand will form a steric block to limit the access and assembly of ribosome to the RNA molecule, thus effectively preventing the translation of TRPV4 RNA. An interfering RNA preferably has the sequence of SEQ ID NO. 3 to 6

Calcium Channel Blocker Specific to TRPV4

Calcium channel blocker specific to TRPV4 that has been used for clinical treatment of hypertension or know antagonists of TRPV4. May include the following: 2-Methyl-1-[3-(4-morpholinyl)propyl]-5-phenyl-N-[3-(trifluoromethyl)phenyl]-1H-pyrrole-3-carboxamide is a potent and selective TRPV4 antagonist. Reversibly inhibits currents through mouse, human and rat TRPV4 orthologs ($IC_{50}$ values are 17, 48 and 133 nM). Also inhibits the endogenous TRPV4-mediated response to 4α-PDH ($IC_{50}$=22 nM). Having a general structure of formula 1

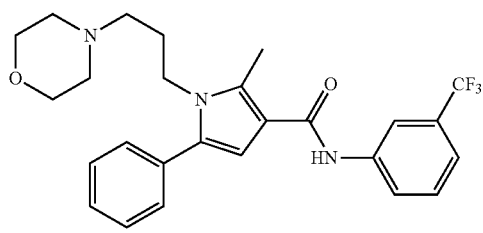

Formula 1

Molecular. Weight:

471.51

$C_{26}H_{28}F_3N_3O_2$  Formula:

Solubility:

Soluble to 100 mM in DMSO and to 25 mM in ethanol

Ruthenium red, is another known inhibitor of TRPV4 as depicted in formula 2

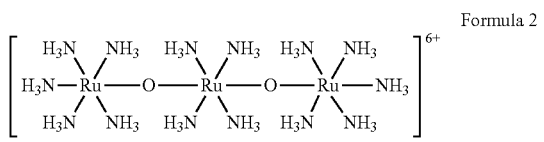

Formula 2

An alternative TRPV4 antagonist is known as depicted in formula 3 it is a compound that reduces 4α-phorbol 12,13-didecanoate (4α-PDD)-induced $Ca^{2+}$ responses,

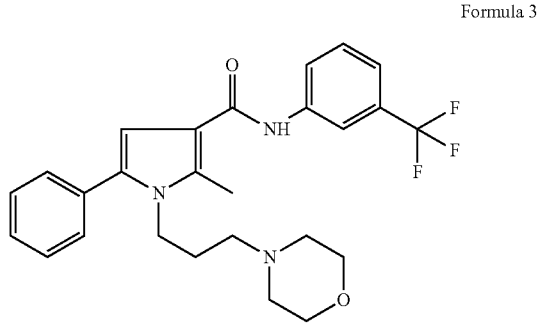 [SMILES: Cc1c(C(=O)Nc2cccc(C(F)(F)F)c2)cc(-c2ccccc2)n1CCCN1CCOCC1]

Formula 3

Any methods capable of knocking down or out transcription or translation of TRPV4 would act as a suitable TRPV4 antagonist such as siRNA of TRPV4 or antisence technology.

Method of Treatment and or Use of the Antagonists

The present invention also provides a method of treating a patient to at least affect a proliferative disorder, which comprises the step of: contacting a cell with an antagonist such as (a) an antibody specific to TRPV4 or (b) an antisence technology specific to TRPV4 or (c) a calcium channel blocker specific to TRPV4. Preferably, the antagonist interferes with metatsesis by means that neutralize Calcium channel blocker specific to TRPV4 expression or activity.

An alternative form of the present invention resides in the use of an antagonist to Calcium channel blocker specific to TRPV4 for the treatment of cancer, preferably the use at least affects cancer cell migration.

Cancer may include, all types of known tumors that exhibit over expression of Calcium channel blocker specific to TRPV4. Cancer metastasis includes cells exhibiting increased TRPV4 expression. Cell proliferating or tumor refers to cells that are growing uncontrollably.

"Treatment" and "treat" and synonyms thereof refer to therapeutic treatment wherein the object is to prevent or slow down (lessen) a tumor or reduce metastasis. Treatment may include prophylactic passive immunization or immunotherapy treatment of a patent. Those in need of such treatment include those with a proliferative disorder.

As used herein a "therapeutically effective amount" of a compound will be an amount of active agent that is capable of preventing or at least slowing down (lessening) cancer cell migration or metastases. Dosages and administration of an antagonist of the invention in a pharmaceutical composition may be determined by one of ordinary skill in the art of clinical pharmacology or pharmacokinetics. An effective amount of the antagonist to be employed therapeutically, for example an antibody, will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng/kg to up to 100 mg/kg of the mammal's body weight or more per day, preferably about 1 µg/kg/day to 10 mg/kg/day. Doses may include an antibody amount anywhere in the range of 0.1 to 20 mg/kg of bodyweight or more preferably 1, 5, 10 mg/kg of bodyweight.

Compositions of the Invention

Thus, the present invention also relates to compositions including pharmaceutical compositions comprising a therapeutically effective amount of (a) an antibody specific to TRPV4 or (b) an antisence technology specific to TRPV4 or (c) a calcium channel blocker specific to TRPV4. As used herein a compound will be therapeutically effective if it is able to affect cancer cell metastases.

Pharmaceutical forms of the invention suitable for injectable use, include sterile aqueous solutions such as sterile phosphate-buffered saline (where water soluble) or dispersions and sterile powders for the extemporaneous preparation of sterile injectable solutions and or one or more carrier. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

The active ingredient may be held within a matrix which controls the release of the active agent. Preferably, the matrix comprises a substance selected from the group consisting of lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and combinations thereof and other polymers Preferably, the matrix sustainedly releases the antibody.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

Polypeptides

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art.

TABLE 1

A list showing genes with differential amount of phosphorylated proteins across the breast cancer metastasis model. 67NR is cancerous but cannot perform any metastatic process, 168FARN can intravasate but not extravasate. 4T07 can intravasate and extravasate but not establish distant colonies. 4T1 can complete all steps of metastasis in animal model.

| | Protein Name | Accession Number | Ratio (168F/67NR) | Ratio (4T07/67NR) | Ratio (4T1/67NR) | P-value (168F/67NR) | P-value (4T07/67NR) | P-value (4T1/67NR) | iTRAQ Peptide |
|---|---|---|---|---|---|---|---|---|---|
| Mild (6) | LOC675857 similar to valosin isoform 1 | IPI00676914 | 0.756 | 1.040 | 0.952 | 5.85423E-12 | 0.486954687 | 0.379843601 | 77 |
| | Epb4.1l2 Protein 4.1G | IPI00402933 | 0.741 | 0.793 | 1.128 | 0.006079954 | 0.09880537 | 0.602683131 | 4 |
| | Wbp2 WW domain binding protein 2 | IPI00648905 | 0.602 | 1.001 | 0.844 | 0.031628469 | 0.997334259 | 0.126308433 | 3 |
| | Centb2 Isoform 1 of Centaurin-beta-2 | IPI00867895 | 1.787 | 1.012 | 1.015 | 0.002997068 | 0.975297188 | 0.69370746 | 2 |
| | LOC100047237 similar to solute carrier family 12, member 2 | IPI00755909 | 1.404 | 1.202 | 0.868 | 0.185737997 | 0.577540722 | 0.684506645 | 2 |
| | Ppfibp1 Isoform 1 of Liprin-beta-1 | IPI00623401 | 1.398 | 0.952 | 0.911 | 8.44658E-13 | 0.87558825 | 0.424489189 | 2 |
| Mild + Moderate (6) | Mtap1b Microtubule-associated protein 1B | IPI00130920 | 1.332 | 0.614 | 0.774 | 0.109536487 | 8.39144E-06 | 0.395215588 | 3 |
| | Eps8 Lung RCB-0558 LLC cDNA, Riken full-length enriched library, clone: G73 | IPI00762437 | 1.810 | 2.175 | 1.226 | 3.32787E-11 | 1.96547E-06 | 0.014567458 | 10 |
| | Sec23b Protein transport protein Sec23B | IPI00317604 | 1.938 | 2.104 | 1.099 | 0.016684461 | 0.016698906 | 0.570911278 | 5 |
| | Ifitm3 10 day old male pancreas cDNA, RIKEN full-length enriched library, | IPI00133243 | 1.609 | 2.227 | 0.958 | 0.053926318 | 0.143767935 | 0.839049685 | 4 |
| | LOC100047481 similar to SEC24 related gene family, member 8 | IPI00652925 | 2.029 | 2.279 | 0.962 | 0.168668401 | 0.11635395 | 0.892921323 | 2 |
| | Inpp1l Phosphatidylinositol-3,4,5-trisphosphate 5-phosphatase-2 | IPI00312067 | 1.402 | 1.527 | 0.843 | 5.22185E-05 | 0.166855705 | 0.740013959 | 2 |
| Moderate (15) | Rasa1 RAS p21 protein activator 1 | IPI00130621 | 0.810 | 0.742 | 1.103 | 0.003832615 | 0.002238603 | 0.004945104 | 2 |
| | Hspa5 78 kDa glucose-regulated protein precursor | IPI00319992 | 1.095 | 1.990 | 1.041 | 0.19073244 | 1.1554E-09 | 0.566297708 | 13 |
| | Syncrip Isoform 2 of Heterogeneous nuclear ribonucleoprotein Q | IPI00406118 | 1.188 | 1.756 | 1.143 | 0.01286025 | 1.70838E-08 | 0.287536417 | 5 |
| | Eef1a1 Elongation factor 1-alpha 1 | IPI00307837 | 1.299 | 1.769 | 1.015 | 0.01768627 | 0 | 0.10305879 | 2 |
| | Plcb3 Osteoclast-like cell cDNA, RIKEN full-length enriched library, clone | IPI00331519 | 1.015 | 1.389 | 0.883 | 0.225475697 | 8.95217E-12 | 0.424728353 | 2 |
| | Plcg1 Phospholipase C, gamma 1 | IPI00753388 | 0.910 | 1.733 | 1.089 | 0.512303556 | 0.15819668 | 0.468633179 | 4 |
| | Bicd2 Isoform 1 of Protein bicaudal D homolog 2 | IPI00274647 | 0.985 | 1.329 | 0.830 | 0.945299747 | 0.201858138 | 0.643246183 | 3 |
| | Cnn3 Calponin-3 | IPI00119111 | 0.926 | 1.567 | 1.049 | 7.3843E-05 | 0.000154769 | 0.667415257 | 2 |
| | Pscd2 Isoform 1 of Cytohesin-2 | IPI00128134 | 1.213 | 1.790 | 1.237 | 0.107920183 | 0.082214853 | 0.138354357 | 3 |
| | Eif3a; ENSMUSG00000074740 Eukaryotic | IPI00129276 | 1.174 | 1.591 | 0.917 | 0.019631331 | 3.63893E-05 | 0.698236763 | 2 |

TABLE 1-continued

A list showing genes with differential amount of phosphorylated proteins across the breast cancer metastasis model. 67NR is cancerous but cannot perform any metastatic process, 168FARN can intravasate but not extravasate. 4T07 can intravasate and extravasate but not establish distant colonies. 4T1 can complete all steps of metastasis in animal model.

| Category | Description | IPI | v1 | v2 | v3 | p1 | p2 | p3 | n |
|---|---|---|---|---|---|---|---|---|---|
| | translation initiation factor 3 subuni | | | | | | | | |
| | Pard3 Par-3 (Partitioning defective 3) homolog | IPI00309259 | 0.798 | 1.323 | 1.300 | 3.67612E-05 | 0 | 0.101034206 | 3 |
| | Pabpc1 Bone marrow macrophage cDNA, RIKEN full-length enriched library, clone | IPI00331552 | 1.108 | 1.866 | 1.028 | 0.124462835 | 6.08289E-06 | 0.903825373 | 2 |
| | GM1821; Rps27a; Ubb; Ubc; LOC100048669; EG619900 ribosomal protein 527a | IPI00470152 | 1.191 | 1.414 | 0.878 | 0.605641691 | 2.02482E-08 | 0.125255398 | 2 |
| | Ewsr1 Ewing sarcoma homolog | IPI00515199 | 0.924 | 1.636 | 0.819 | 0.905828669 | 0.536744723 | 0.679221255 | 2 |
| | Cadm2 Isoform 1 of Cell adhesion molecule 2 precursor | IPI00850457 | 1.049 | 2.249 | 1.073 | 0.717642878 | 0 | 0.40510054 | 2 |
| Moderate + Aggressive (7) | Lgals3 NOD-derived CD11c +ve dendritic cells cDNA, RIKEN full-length enric | IPI00224486 | 1.009 | 0.593 | 0.400 | 0.954869229 | 0.123601419 | 0.000338827 | 3 |
| | Ctnnd1 99 kDa protein | IPI00663949 | 0.919 | 1.430 | 2.378 | 0.222173997 | 4.42515E-05 | 0 | 30 |
| | Hsp70-71 kDa protein | IPI00457741 | 1.251 | 1.783 | 1.376 | 0.000375468 | 0.02137714 | 0.028749843 | 9 |
| | Tubb5 Tubulin beta-5 chain | IPI00117352 | 1.196 | 1.919 | 1.336 | 0.124397609 | 0.000440143 | 0.004405411 | 12 |
| | Baiap2 Isoform 1 of Brain-specific angiogenesis inhibitor 1-associated pro | IPI00222731 | 1.244 | 1.633 | 2.253 | 0.1694422 | 0.047365687 | 0.065972063 | 6 |
| | Trpv4 91 kDa protein | IPI00776323 | 0.938 | 2.514 | 1.941 | 0.20933523 | 0 | 2.58039E-07 | 3 |
| | Hgs Mammary gland RCB-0526 lyg-MC(A) cDNA, RIKEN full-length enriched library | IPI00649267 | 1.126 | 1.382 | 1.319 | 0.178240693 | 0 | 9.81761E-06 | 2 |
| Aggressive (12) | Lrp1 Prolow-density lipoprotein receptor-related protein 1 precursor | IPI00119063 | 0.854 | 0.801 | 0.538 | 0.000748878 | 0.059456543 | 8.39504E-10 | 5 |
| | Nckap1 Isoform 2 of Nck-associated protein 1 | IPI00656204 | 0.803 | 1.024 | 0.751 | 23939E-23 | 0.819514298 | 2.16296E-30 | 4 |
| | Actn1 Alpha-actinin-1 | IPI00380436 | 1.036 | 0.776 | 0.704 | 0.756834983 | 0.157048651 | 0.195645117 | 4 |
| | Fus Fusion, derived from t(12;16) malignant liposarcoma | IPI00830623 | 1.205 | 1.281 | 0.713 | 0.000776729 | 0.305870656 | 0.041995508 | 3 |
| | Rab7 Ras-related protein Rab-7a | IPI00408892 | 0.991 | 0.819 | 0.452 | 0.961611266 | 0.484404367 | 0.00034121 | 3 |
| | Actn4 Alpha-actinin-4 | IPI00118899 | 1.084 | 0.840 | 0.699 | 0.277506402 | 0.306468733 | 0.18506059 | 4 |
| | Slc12a4 Bone marrow macrophage cDNA, RIKEN full-length enriched library, clone | IPI00115231 | 0.860 | 0.955 | 0.684 | 0.579823007 | 0.375617912 | 0.254010111 | 2 |
| | Mllt4 Isoform 1 of Afadin | IPI00853902 | 0.946 | 0.943 | 1.335 | 0.336009236 | 0.586390232 | 3.30049E-08 | 9 |
| | Dbnl Isoform 1 of Drebrin-like protein | IPI00378015 | 1.140 | 1.260 | 1.341 | 0.11107079 | 1.36877E-06 | 0.000117084 | 8 |
| | Tjp2 Tight junction protein ZO-2 | IPI00323349 | 0.995 | 1.215 | 3.078 | 0.941353016 | 0.07981033 | 0.009752445 | 8 |
| | Bcar1 Isoform Cas-A of Breast cancer anti-estrogen resistance protein 1 | IPI00230632 | 1.002 | 1.238 | 1.671 | 0.989232344 | 0.009817961 | 1.23843E-10 | 4 |

TABLE 1-continued

A list showing genes with differential amount of phosphorylated proteins across the breast cancer metastasis model. 67NR is cancerous but cannot perform any metastatic process, 168FARN can intravasate but not extravasate. 4TO7 can intravasate and extravasate but not establish distant colonies. 4T1 can complete all steps of metastasis in animal model.

| | | | | | | | | | |
|---|---|---|---|---|---|---|---|---|---|
| | Dsg2 desmoglein 2 | IPI00877308 | 1.069 | 1.180 | 5.492 | 0.55491106 | 0.01432624 | 0.013971353 | 2 |
| Mild + Aggressive (2) | Prkcd Isoform 2 of Protein kinase C delta type | IPI00227880 | 0.714 | 0.969 | 1.610 | 0 | 0.050031135 | 0.00471921 | 2 |
| | Hspa9 heat shock protein 9 | IPI00880839 | 1.396 | 0.955 | 0.688 | 0.104538732 | 0.436580618 | 5.83553E-05 | 2 |
| Mild + Moderate + Aggressive (12) | Epb4.1/3 Isoform 2 of Band 4.1-like protein 3 | IPI00229294 | 0.436 | 0.326 | 0.272 | 1.59038E-21 | 1.80483E-44 | 2.1136E-122 | 3 |
| | Pvrl3 Isoform 2 of Poliovirus receptor-related protein 3 precursor | IPI00227826 | 0.476 | 0.556 | 0.370 | 0.004611914 | 0.008798892 | 0.000415779 | 2 |
| | Ctnnb1 Adult male pituitary gland cDNA, RIKEN full-length enriched library | IPI00753025 | 0.506 | 0.569 | 2.157 | 1.11672E-26 | 1.18891E-14 | 2.62984E-07 | 6 |
| | Pxn Isoform Beta of Paxillin | IPI00165881 | 0.688 | 1.537 | 1.684 | 0.07536715 | 0.009555154 | 0.051119388 | 4 |
| | Ezr; LOC100044177 Ezrin | IPI00330862 | 2.131 | 2.430 | 3.046 | 2.78417E-07 | 5.94518E-09 | 0.001629193 | 11 |
| | Plcg2 13 days embryo heart cDNA, RIKEN full-length enriched library, clone | IPI00229848 | 2.162 | 1.772 | 2.646 | 0.02300668 | 0.02246284 | 0.039297795 | 7 |
| | Sec31a Isoform 2 of Protein transport protein Sec31A | IPI00853859 | 2.571 | 2.526 | 1.397 | 0.172538865 | 0.142472758 | 0.151079351 | 6 |
| | Tuba1b Tubulin alpha-1B chain | IPI00117348 | 1.364 | 1.819 | 1.402 | 5.74341E-12 | 8.13733E-06 | 0.119400359 | 5 |
| | Cdh1 Epithelial cadherin precursor | IPI00318626 | 1.406 | 1.313 | 2.701 | 0.06442269 | 4.14034E-10 | 0.035278251 | 2 |
| | Emd TTB-55 BB88 cDNA, RIKEN full-length enriched library, clone: I730066M18 | IPI00652858 | 1.726 | 2.942 | 1.785 | 0.095593742 | 6.63869E-12 | 0.007053035 | 3 |
| | Lasp1 LIM and SH3 protein 1 | IPI00648086 | 1.475 | 1.447 | 1.866 | 0.00762348 | 2.88658E-15 | 6.79864E-05 | 2 |
| | Sec24a SEC24 related gene family, member A | IPI00831587 | 2.144 | 2.554 | 1.316 | 0.086216513 | 0.012249084 | 0 | 2 |

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The present application contains a Sequence Listing that was submitted electronically in ASCII format and is hereby incorporated by reference in its entirety. The ASCII file, created on Feb. 25, 2014, is named S150770109US00-SEQLIST-JRV.txt and has a size of 12378 bytes.

The invention claimed is:

1. A method of treating breast cancer metastasis in a patient having elevated levels of TRPV4 in invasive breast cancer epithelial cells relative to non-invasive breast cancer epithelial cells, the method comprising administering to the patient an antagonist to TRPV4 nucleic acid expression or polypeptide activity in amount effective to inhibit, respectively, TRPV4 nucleic acid expression or polypeptide activity in breast cancer epithelial cells, wherein the antagonist is a TRPV4 interfering RNA or a calcium channel blocker specific to TRPV4.

2. The method of claim 1 wherein the antagonist is 2-Methyl-1-[3-(4-morpholinyl)propyl]-5-phenyl-N-[3-(trifluoromethyl)phenyl]-1H-pyrrole-3-carboxamide having the general structure of Formula 1:

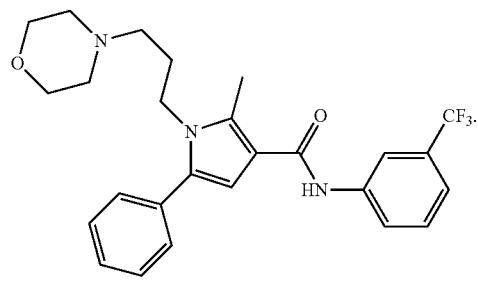

Formula 1

3. The method of claim 1 wherein the antagonist is ruthenium red having the general structure of Formula 2:

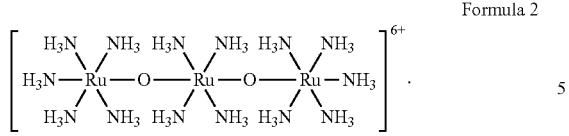
Formula 2
4. The method of claim 1 wherein the antagonist is a compound that reduces TRPV4 responses to 4α-phorbol 12,13-didecanoate (4α-PDD)-induced $Ca^{2+}$, the compound having the general structure of Formula 3:
Formula 3
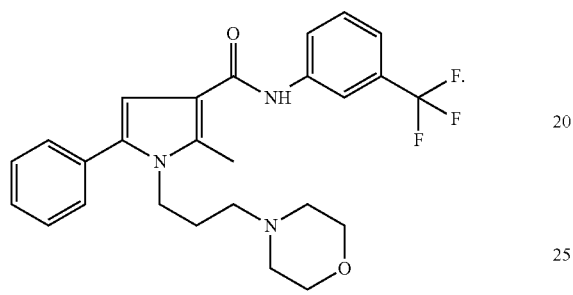
* * * * *

SEQUENCE LISTING

```
<160> NUMBER OF SEQ ID NOS: 6

<210> SEQ ID NO 1
<211> LENGTH: 2843
<212> TYPE: DNA
<213> ORGANISM: Homo sapiens

<400> SEQUENCE: 1
atggcggatt ccagcgaagg cccccgcgcg gggcccgggg aggtggctga gctccccggg      60
gatgagagtg gcaccccagg tggggaggct tttcctctct cctccctggc caatctgttt     120 gaggggagg atggctccct ttcgccctca ccggctgatg ccagtcgccc tgctggccca     180
ggcgatgggc gaccaaatct gcgcatgaag ttccagggcg ccttccgcaa gggggtgccc     240
aaccccatcg atctgctgga gtccaccta tatgagtcct cggtggtgcc tgggcccaag     300
aaagcaccca tggactcact gtttgactac ggcacctatc gtcaccactc cagtgacaac     360
aagaggtgga ggaagaagat catagagaag cagccgcaga gccccaaagc tcccgcccct     420
cagccgcccc ccatcctcaa agtcttcaac cggcccatcc tctttgacat cgtgtcccgg     480
ggctccactg ctgacctgga cgggctgctc ccattcttgc tgacccacaa gaaacgccta     540
actgatgagg agtttcggga accatctacg gggaagacct gcctgcccaa ggccttgctg     600
aacctgagca atggccgcaa cgacaccatc cctgtgctgc tggacatcgc ggagcgcacc     660
ggcaacatga gggagttcat taactcgccc ttccgtgaca tctactatcg agggcagaca     720
gccctgcaca tcgccattga gcgtcgctgc aaacactacg tggaacttct cgtggcccag     780
ggagctgatg tccacgccca ggcccgtggg cgcttcttcc agcccaagga tgaggggggc     840
tacttctact ttgggagct gccctgtcg ctggctgcct gcaccaacca gccccacatt     900
gtcaactacc tgacggagaa cccccacaag aaggcggaca tgcggcgcca ggactcgcga     960
```

| | | | | |
|---|---|---|---|---|
| ggcaacacag | tgctgcatgc | gctggtggcc | attgctgaca | caccccgtga gaacaccaag | 1020 |
| tttgttacca | agatgtacga | cctgctgctg | ctcaagtgtg | cccgcctctt ccccgacagc | 1080 |
| aacctggagg | ccgtgctcaa | caacgacggc | ctctcgcccc | tcatgatggc tgccaagacg | 1140 |
| ggcaagattg | gggtctttca | gcacatcatc | cggcggagg | tgacggatga ggacacacgg | 1200 |
| cacctgtccc | gcaagttcaa | ggactgggcc | tatgggccag | tgtattcctc gctttatgac | 1260 |
| ctctcctccc | tggacacgtg | tggggaagag | gcctccgtgc | tggagatcct ggtgtacaac | 1320 |
| agcaagattg | agaaccgcca | cgagatgctg | gctgtggagc | ccatcaatga actgctgcgg | 1380 |
| gacaagtggc | gcaagttcgg | ggccgtctcc | ttctacatca | acgtggtctc ctacctgtgt | 1440 |
| gccatggtca | tcttcactct | caccgcctac | taccagccgc | tggagggcac accgccgtac | 1500 |
| ccttaccgca | ccacggtgga | ctacctgcgg | ctggctggcg | aggtcattac gctcttcact | 1560 |
| ggggtcctgt | tcttcttcac | caacatcaaa | gacttgttca | tgaagaaatg ccctggagtg | 1620 |
| aattctctct | tcattgatgg | ctccttccag | ctgctctact | tcatctactc tgtcctggtg | 1680 |
| atcgtctcag | cagccctcta | cctggcaggg | atcgaggcct | acctggccgt gatggtcttt | 1740 |
| gccctggtcc | tgggctggat | gaatgccctt | tacttcaccc | gtgggctgaa gctgacgggg | 1800 |
| acctatagca | tcatgatcca | gaagattctc | ttcaaggacc | ttttccgatt cctgctcgtc | 1860 |
| tacttgctct | tcatgatcgg | ctacgcctca | gccctggtct | ccctcctgaa cccgtgtgcc | 1920 |
| aacatgaagg | tgtgcaatga | ggaccagacc | aactgcacag | tgcccactta ccctcgtgc | 1980 |
| cgtgacagcg | agaccttcag | caccttcctc | ctggacctgt | ttaagctgac catcggcatg | 2040 |
| ggcgacctgg | agatgctgag | cagcaccaag | taccccgtgg | tcttcatcat cctgctggtg | 2100 |
| acctacatca | tcctcacctt | tgtgctgctc | ctcaacatgc | tcattgccct catgggcgag | 2160 |
| acagtgggcc | aggtctccaa | ggagagcaag | cacatctgga | agctgcagtg ggccaccacc | 2220 |
| atcctggaca | ttgagcgctc | cttccccgta | ttcctgagga | aggccttccg ctctggggag | 2280 |
| atggtcaccg | tgggcaagag | ctcggacggc | actcctgacc | gcaggtggtg cttcagggtg | 2340 |
| aatgaggtga | actggtctca | ctggaaccag | aacttgggca | tcatcaacga ggacccgggc | 2400 |
| aagaatgaga | cctaccagta | ttatggcttc | tcgcataccg | tgggccgcct ccgcagggat | 2460 |
| cgctggtcct | cggtggtacc | ccgcgtggtg | gaactgaaca | agaactcgaa cccggacgag | 2520 |
| gtggtggtgc | ctctggacag | catggggaac | cccgctgcg | atggccacca gcagggttac | 2580 |
| ccccgcaagt | ggaggactga | tgacgccccg | ctctagggac | tgcagcccag ccccagcttc | 2640 |
| tctgccccact | catttctagt | ccagccgcat | ttcagcagtg | ccttctgggg tgtcccccca | 2700 |
| cacccctgctt | tggccccaga | ggcgagggac | cagtggaggt | gccagggagg ccccaggacc | 2760 |
| ctgtggtccc | ctggctctgc | ctccccaccc | tgggggtgggg | gctcccggcc acctgtcttg | 2820 |
| ctcctatgga | gtcacataag | cca | | | 2843 |

<210> SEQ ID NO 2
<211> LENGTH: 871
<212> TYPE: PRT
<213> ORGANISM: Homo sapiens

<400> SEQUENCE: 2

Met Ala Asp Ser Ser Glu Gly Pro Arg Ala Gly Pro Gly Glu Val Ala
1               5                   10                  15

Glu Leu Pro Gly Asp Glu Ser Gly Thr Pro Gly Gly Glu Ala Phe Pro
            20                  25                  30

```
Leu Ser Ser Leu Ala Asn Leu Phe Glu Gly Glu Asp Gly Ser Leu Ser
         35                  40                  45

Pro Ser Pro Ala Asp Ala Ser Arg Pro Ala Gly Pro Gly Asp Gly Arg
 50                  55                  60

Pro Asn Leu Arg Met Lys Phe Gln Gly Ala Phe Arg Lys Gly Val Pro
 65                  70                  75                  80

Asn Pro Ile Asp Leu Leu Glu Ser Thr Leu Tyr Glu Ser Ser Val Val
             85                  90                  95

Pro Gly Pro Lys Lys Ala Pro Met Asp Ser Leu Phe Asp Tyr Gly Thr
            100                 105                 110

Tyr Arg His His Ser Ser Asp Asn Lys Arg Trp Arg Lys Lys Ile Ile
            115                 120                 125

Glu Lys Gln Pro Gln Ser Pro Lys Ala Pro Ala Pro Gln Pro Pro Pro
        130                 135                 140

Ile Leu Lys Val Phe Asn Arg Pro Ile Leu Phe Asp Ile Val Ser Arg
145                 150                 155                 160

Gly Ser Thr Ala Asp Leu Asp Gly Leu Leu Pro Phe Leu Leu Thr His
                165                 170                 175

Lys Lys Arg Leu Thr Asp Glu Glu Phe Arg Glu Pro Ser Thr Gly Lys
                180                 185                 190

Thr Cys Leu Pro Lys Ala Leu Leu Asn Leu Ser Asn Gly Arg Asn Asp
            195                 200                 205

Thr Ile Pro Val Leu Leu Asp Ile Ala Glu Arg Thr Gly Asn Met Arg
210                 215                 220

Glu Phe Ile Asn Ser Pro Phe Arg Asp Ile Tyr Tyr Arg Gly Gln Thr
225                 230                 235                 240

Ala Leu His Ile Ala Ile Glu Arg Arg Cys Lys His Tyr Val Glu Leu
                245                 250                 255

Leu Val Ala Gln Gly Ala Asp Val His Ala Gln Ala Arg Gly Arg Phe
                260                 265                 270

Phe Gln Pro Lys Asp Glu Gly Gly Tyr Phe Tyr Phe Gly Glu Leu Pro
            275                 280                 285

Leu Ser Leu Ala Ala Cys Thr Asn Gln Pro His Ile Val Asn Tyr Leu
            290                 295                 300

Thr Glu Asn Pro His Lys Lys Ala Asp Met Arg Arg Gln Asp Ser Arg
305                 310                 315                 320

Gly Asn Thr Val Leu His Ala Leu Val Ala Ile Ala Asp Asn Thr Arg
                325                 330                 335

Glu Asn Thr Lys Phe Val Thr Lys Met Tyr Asp Leu Leu Leu Leu Lys
            340                 345                 350

Cys Ala Arg Leu Phe Pro Asp Ser Asn Leu Glu Ala Val Leu Asn Asn
            355                 360                 365

Asp Gly Leu Ser Pro Leu Met Met Ala Ala Lys Thr Gly Lys Ile Gly
            370                 375                 380

Ile Phe Gln His Ile Ile Arg Arg Glu Val Thr Asp Glu Asp Thr Arg
385                 390                 395                 400

His Leu Ser Arg Lys Phe Lys Asp Trp Ala Tyr Gly Pro Val Tyr Ser
                405                 410                 415

Ser Leu Tyr Asp Leu Ser Ser Leu Asp Thr Cys Gly Glu Glu Ala Ser
                420                 425                 430

Val Leu Glu Ile Leu Val Tyr Asn Ser Lys Ile Glu Asn Arg His Glu
            435                 440                 445
```

```
Met Leu Ala Val Glu Pro Ile Asn Glu Leu Leu Arg Asp Lys Trp Arg
    450                 455                 460

Lys Phe Gly Ala Val Ser Phe Tyr Ile Asn Val Val Ser Tyr Leu Cys
465                 470                 475                 480

Ala Met Val Ile Phe Thr Leu Thr Ala Tyr Tyr Gln Pro Leu Glu Gly
                485                 490                 495

Thr Pro Pro Tyr Pro Tyr Arg Thr Thr Val Asp Tyr Leu Arg Leu Ala
            500                 505                 510

Gly Glu Val Ile Thr Leu Phe Thr Gly Val Leu Phe Phe Thr Asn
        515                 520                 525

Ile Lys Asp Leu Phe Met Lys Lys Cys Pro Gly Val Asn Ser Leu Phe
    530                 535                 540

Ile Asp Gly Ser Phe Gln Leu Leu Tyr Phe Ile Tyr Ser Val Leu Val
545                 550                 555                 560

Ile Val Ser Ala Ala Leu Tyr Leu Ala Gly Ile Glu Ala Tyr Leu Ala
                565                 570                 575

Val Met Val Phe Ala Leu Val Leu Gly Trp Met Asn Ala Leu Tyr Phe
            580                 585                 590

Thr Arg Gly Leu Lys Leu Thr Gly Thr Tyr Ser Ile Met Ile Gln Lys
        595                 600                 605

Ile Leu Phe Lys Asp Leu Phe Arg Phe Leu Leu Val Tyr Leu Leu Phe
    610                 615                 620

Met Ile Gly Tyr Ala Ser Ala Leu Val Ser Leu Leu Asn Pro Cys Ala
625                 630                 635                 640

Asn Met Lys Val Cys Asn Glu Asp Gln Thr Asn Cys Thr Val Pro Thr
                645                 650                 655

Tyr Pro Ser Cys Arg Asp Ser Glu Thr Phe Ser Thr Phe Leu Leu Asp
            660                 665                 670

Leu Phe Lys Leu Thr Ile Gly Met Gly Asp Leu Glu Met Leu Ser Ser
        675                 680                 685

Thr Lys Tyr Pro Val Val Phe Ile Ile Leu Leu Val Thr Tyr Ile Ile
    690                 695                 700

Leu Thr Phe Val Leu Leu Leu Asn Met Leu Ile Ala Leu Met Gly Glu
705                 710                 715                 720

Thr Val Gly Gln Val Ser Lys Glu Ser Lys His Ile Trp Lys Leu Gln
                725                 730                 735

Trp Ala Thr Thr Ile Leu Asp Ile Glu Arg Ser Phe Pro Val Phe Leu
            740                 745                 750

Arg Lys Ala Phe Arg Ser Gly Glu Met Val Thr Val Gly Lys Ser Ser
        755                 760                 765

Asp Gly Thr Pro Asp Arg Arg Trp Cys Phe Arg Val Asp Glu Val Asn
    770                 775                 780

Trp Ser His Trp Asn Gln Asn Leu Gly Ile Ile Asn Glu Asp Pro Gly
785                 790                 795                 800

Lys Asn Glu Thr Tyr Gln Tyr Tyr Gly Phe Ser His Thr Val Gly Arg
                805                 810                 815

Leu Arg Arg Asp Arg Trp Ser Ser Val Val Pro Arg Val Val Glu Leu
            820                 825                 830
```

```
Asn Lys Asn Ser Asn Pro Asp Glu Val Val Pro Leu Asp Ser Met
        835                 840                 845

Gly Asn Pro Arg Cys Asp Gly His Gln Gln Gly Tyr Pro Arg Lys Trp
850                 855                 860

Arg Thr Asp Asp Ala Pro Leu
865                 870

<210> SEQ ID NO 3
<211> LENGTH: 25
<212> TYPE: DNA
<213> ORGANISM: Artificial Sequence
<220> FEATURE:
<223> OTHER INFORMATION: TRPV4 mouse siRNA1

<400> SEQUENCE: 3
agaagcagca ggucguacau cuugg                                  25

<210> SEQ ID NO 4
<211> LENGTH: 25
<212> TYPE: DNA
<213> ORGANISM: Artificial Sequence
<220> FEATURE:
<223> OTHER INFORMATION: TRPV4 mouse siRNA3

<400> SEQUENCE: 4
aaacuuggug uucucucggg uguug                                  25

<210> SEQ ID NO 5
<211> LENGTH: 25
<212> TYPE: DNA
<213> ORGANISM: Artificial Sequence
<220> FEATURE:
<223> OTHER INFORMATION: TRPV4 human siRNA1

<400> SEQUENCE: 5
ggggaagagg cgggcacacu ugagc                                  25

<210> SEQ ID NO 6
<211> LENGTH: 25
<212> TYPE: DNA
<213> ORGANISM: Artificial Sequence
<220> FEATURE:
<223> OTHER INFORMATION: TRPV4 human siRNA3

<400> SEQUENCE: 6
gcaggucgua caucuuggua acaaa                                  25
```